United States Patent [19]

Giovanni

[11] Patent Number: 4,941,468

[45] Date of Patent: Jul. 17, 1990

[54] REGULATOR FOR BREATHING APPARATUS

[75] Inventor: Garofalo Giovanni, Rapallo, Italy

[73] Assignee: AMF MARES S.p.A., Italy

[21] Appl. No.: 352,247

[22] Filed: May 16, 1989

[30] Foreign Application Priority Data

Jun. 8, 1988 [IT] Italy ............................ 12498 A/88

[51] Int. Cl.[5] ............................ A61M 16/00

[52] U.S. Cl. ............................ 128/204.26; 128/202.27; 128/205.24

[58] Field of Search ............................ 128/201.27, 202.27, 128/204.18, 204.26, 205.24; 441/92, 94; 137/269, 490

[56] References Cited

U.S. PATENT DOCUMENTS

| | | | |
|---|---|---|---|
| 1,788,282 | 1/1931 | Drager | 285/208 |
| 3,563,265 | 2/1971 | Graham | 137/269 |
| 3,570,808 | 3/1971 | Wren | 128/204.26 |
| 3,739,804 | 6/1973 | Dubreuil | 137/269 |
| 4,010,746 | 3/1977 | Pedersen | 128/204.26 |
| 4,029,120 | 6/1977 | Christianson | 128/204.26 |
| 4,076,041 | 2/1978 | Christianson | 128/204.26 |
| 4,147,176 | 4/1979 | Christianson | 128/204.26 |
| 4,214,580 | 7/1980 | Pedersen | 128/204.26 |
| 4,616,645 | 10/1986 | Pedersen et al. | 128/204.26 |
| 4,683,881 | 8/1987 | Hansen et al. | 128/2094.26 |
| 4,798,202 | 1/1989 | Chambonnet | 128/204.26 |
| 4,862,884 | 9/1989 | Christianson | 128/204.26 |

*Primary Examiner*—Edgar S. Burr
*Assistant Examiner*—Aaron J. Lewis
*Attorney, Agent, or Firm*—Larson and Taylor

[57] ABSTRACT

The invention relates to a regulator for breathing apparatus with a first reducing stage and a second reducing stage (2, 6) integral with a moutpiece (4) comprising a chamber (2) communicating with the mouthpiece (4) and a chamber (6) communicating with the surroundings, separated by a membrane (5) which controls the opening and the closure of a dispensing valve provided in a connector member (10) between the first and second stages. To premit the connector member (10) to be mounted in a reliable and easy manner, either on the right-hand and left-hand sides of the second stage of a regulator for a breathing apparatus, the chamber (2) communicating with the mouthpiece (4) is provided both on the right-hand and left-hand sides with a mating seat (9) for the connector member (10) between the two stages and said member (10) has two dispensing holes (15) of the same size, a closing and/or throttling means (11) for the dispensing hole (15) away from the mouthpiece (4) being provided at each mating seat (9).

10 Claims, 3 Drawing Sheets 10
21
18
20
19
16
17
9
15
15
8
11
111
12
112
14
12
112
7
4
2
111
9
11
16
18
19
22
117

REGULATOR FOR BREATHING APPARATUS

FIELD OF THE INVENTION

The invention relates to a regulator for breathing apparatus with a first reducing stage and a second reducing stage integral with a mouthpiece comprising a chamber communicating with the mouthpiece and a chamber communicating with the surroundings, separated by a membrane which controls the opening and the closure of a dispensing valve provided in a connector member between the first and second stages.

BACKGROUND OF THE INVENTION

In the known breathing apparatus regulators of this type, the connector member between the two stages is connected to the second stage on either the right-hand or left-hand side. However, in many circumstances, it would be advantageous to be able to change the position of said connector member. With the conventional regulators, the above cannot be carried out in a simple manner. From FR-A-2 285 155 a regulator is known comprising a tapped union for the connector member both on the right-hand and on the left-hand sides, but the transfer of the connector member from one side to the other side must be carried out in a workshop and requires the change of the connector member. Said member, in effect, comprises, usually, two dispensing holes, one of which constitutes the main dispensing hole and is directed towards the mouth-piece, and the other of which—of considerably smaller dimensions—is directed in any other direction and is used so compensate for the Venturi effect generated in the regulator so as to prevent said regulator from shifting into a "self-dispensing" condition.

SUMMARY OF THE INVENTION

The main object of the invention is to provide a regulator of the type described in the preamble and which, by a comparatively simple and economical construction, permits the connector member to be easily displaced between the two stages onto the desired side of the second stage of the regulator, while avoiding the risk of "self-dispensing", and without requiring complicated operations for this purpose.

The invention achieves this object by providing the communication chamber both on the right-hand and left-hand sides, with a mating seat for the connector member between the two stages, and by providing said connector member with two dispensing holes of the same dimensions, a closing and/or throttling means for the dispensing hole away from the mouthpiece being provided by each mating seat.

Moreover, in the chamber communicating with the mouthpiece, in proximity of each of the two mating seats for said connector member, the invention provides, symmetrically with respect to the longitudinal vertical central plane, a baffle to convey the dispensed air directly to the mouthpiece, said baffle extending so as to completely overlay and at a certain distance the mouth of a pipe-union for the mouthpiece, said baffle being formed with slots for passage of a fraction of the air into the chamber communicating with the mouthpiece, so as to avoid "self-dispensing" phenomena.

According to a further characteristic of the invention, the connector member is locked in a pre-established position in its seat by means of a bayonet coupling, centering and safety means being provided to prevent any accidental disconnection of said member.

The invention relates as well to other characteristics which further improve said regulator for breathing apparatus, and which are the subject of the dependent claims.

BRIEF DESCRIPTION OF THE DRAWINGS

The peculiar characteristics of the invention and the advantages resulting therefrom will be apparent with more details from the following description of a preferred embodiment thereof, shown by way of non-limiting example in the accompanying drawings, wherein.

DESCRIPTION OF THE PREFERRED EMBODIMENT OF THE INVENTION

Figure 1:
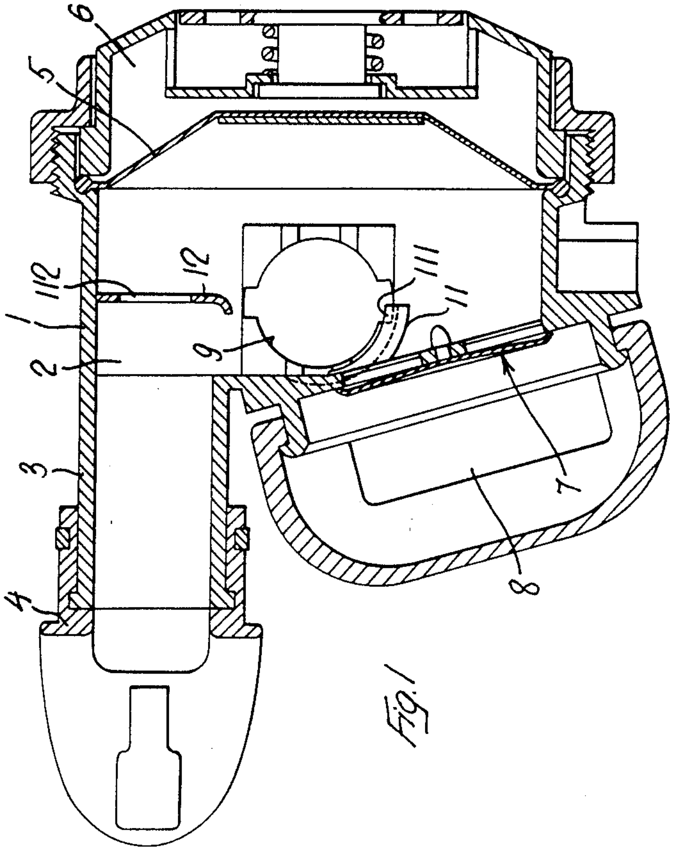
FIG. 1 is a longitudinal sectional view of the second stage of the regulator for breathing apparatus according to the invention, without the connector member to the first stage.

The second stage of the regulator for breathing apparatus, shown in FIG. 1 comprises a substantially cylindrical casing 1 formed with a chamber 2 communicating through a pipe-union 3 with a mouthpiece 4 and separated by a membrane 5 from a chamber 6 communicating with the surroundings. On the same side as the pipe-union 3, the chamber 2 is provided with an outlet valve 7 for the exhaled air, said valve communicating with the intermediate region of a conduit 8 which opens at both sides (right- and left-hand sides) of the casing 1.

Provided on each of the two sides of the casing 1 is a radial union 9 constituting the mating seat for a connector member 10 for connection to the first stage of the regulator (not shown). The two unions 9 are co-axial with each other and are normal to the axis of the casing 1. Each union 9, at the end which opens into the chamber 2, is provided with a co-axial extension lug 11 protruding from the wall of the chamber 2 away from the membrane 5 and extending downwards by approximately one fourth of the perimeter of said union 9. At the free end thereof, said lug 11 ends in a shoulder ledge 111 for the connector member 10.

Figure 3:
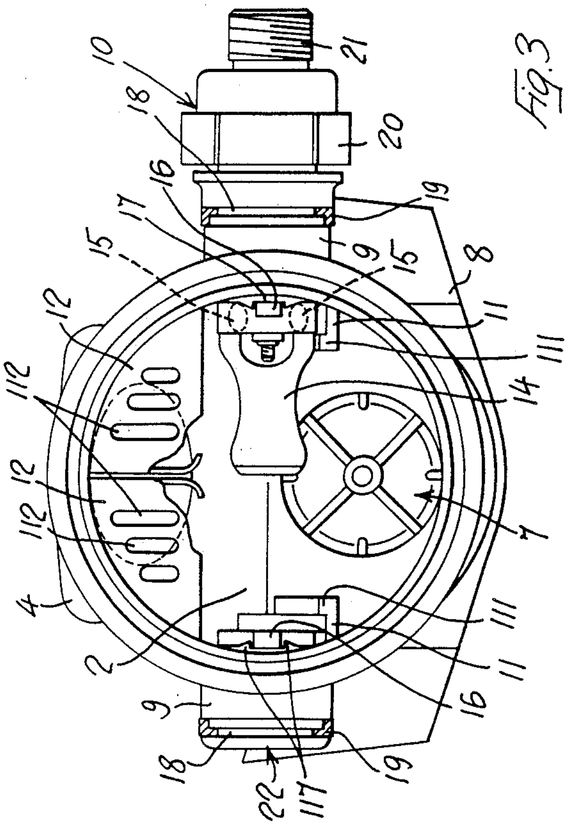
FIG. 3 is a side elevational view of the second stage of the regulator on the side away from the mouthpiece, without the exterior-communicating chamber and without the membrane.

Within the chamber 2, from the upper wall of the casing 1, transversely to the longitudinal axis of said chamber, two co-planar baffle-wings 12 extend downwards and completely overlay the mouth of the union 3 for the mouthpiece 4 and are spaced from said mouth. The lower free ends of said baffle-wings 12 are slightly bent towards the union 3 and extend nearly at the same level as the upper wall of the unions 9 and the lower wall of the union 3. Said baffle wings 12 are symmetrical with respect to the longitudinal intermediate vertical plane of the regulator second stage, and they terminate at a short distance from each other at this plane and are bent towards said union 3 also at these sides (see FIGS. 3 and 4). As appearing particularly from FIGS. 3 and 4), each baffle-wing, 12 is formed with slots, more particularly with three vertical slots 112.

Figure 2:
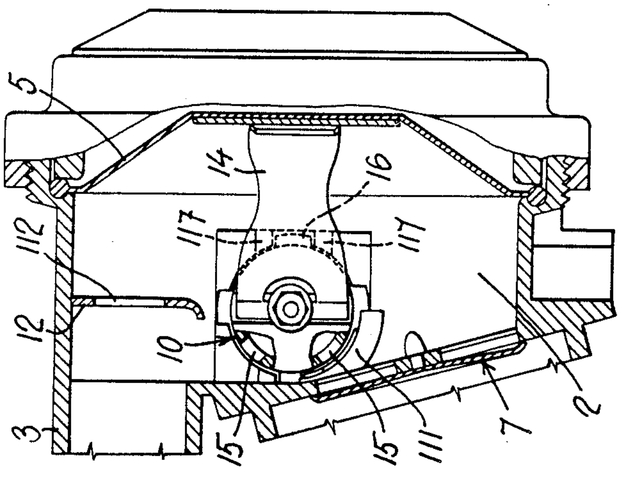
FIG. 2 is a longitudinal sectional view similar to FIG. 1, having the connector member mounted thereon.
Figure 4:
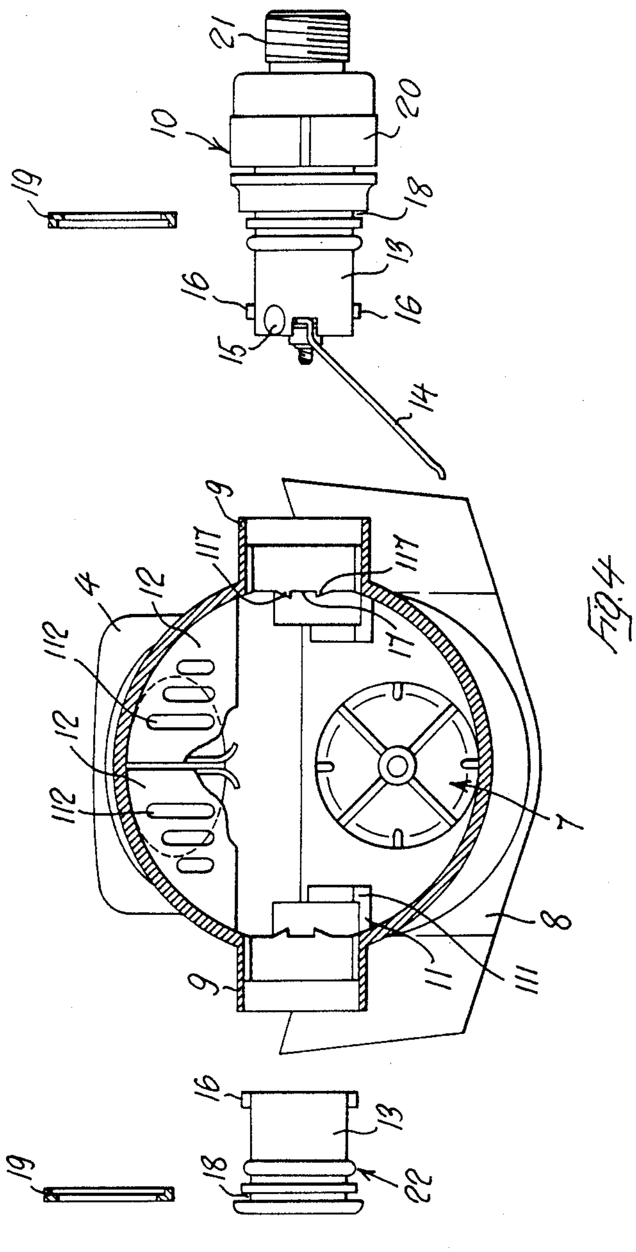
FIG. 4 is a view similar to FIG. 3, the connector member and plug being disengaged.

As is now apparent, particularly from FIG. 4, the connector member 10 comprises at its coupling end a cylindrical portion 13 enclosing a valve which is controlled by a tang 14 which co-operates with the membrane 5 when the connector member 10 is fitted-in (see FIG. 2). Said cylindrical portion 13 comprises also two dispensing holes 15 (see FIGS. 2–3) and two diametrically opposite pegs 16 whereby it can form a bayonet joint in either one of the unions 9. Moreover, the connector member 10 is formed in the portion thereof outside of the unions 9 with a groove 18 to receive an L-shaped sealing ring 19 which, in the coupled position, co-operates with the end face of the associated union 9 (see FIG. 3). It comprises as well a non-round gripping portion 20 and terminates in a threaded portion 21 to be coupled to a pipe for connection to the first stage of the regulator (both not shown).

The bayonet joint of each union 9 comprises a groove 17 defined at both sides by two ridges 117 which are shaped as ratchet teeth and are disposed so that upon coupling the connector member 10 the pegs 16 on the cylindrical portion 13 will slide over the ratchet ridges 117 and snappingly engage into the groove 17. The groove 17 and the holes 15 in the cylindrical portion 13 of the connector member 10 are disposed so that, upon coupling said connector member into either one of the unions 9 of the chamber 2 and upon locking it in position by means of the groove 17, the extension lug 11 of the related union 9 will overlap one of the holes 15 to close it or just throttle it, while the other hole 15 opens into the space between the respective baffle wing 12 and the union 3 of the mouthpiece 4 (see FIGS. 2 and 4). As shown in the FIGS. 3 and 4, the union 9 which is not coupled with the connector member 10 will be closed by means of a plug 22 which, similarly to the connector member 10, comprises a cylindrical portion 13 with two diametrically-opposite pegs 16 and a groove 18 accommodating a sealing ring 19; and it has also a bayonet-fit into the respectively free union 9.

The described particular configuration of the connector member 10 and union 9 enables a simple and reliable connector of said connector member to the chamber 2 by means of a simple and quick operation.

By virtue of the groove 17 co-operating with the pegs 16 on the connector member, the latter is always reliably locked in the proper position and it may be only disengaged by a voluntary action of the user, i.e. by axially depressing the connector member 10 inwards into the chamber 2 to disengage the pegs 16 from the groove 17 of the bayonet joint. Obviously, this is also true for the plug 22.

The particular arrangement of the baffle-wings 12 at each union 9 and with respect to the hole 15 which is respectively directed towards the mouthpiece in the locked position of the connector member 10 permits to achieve an improved and more direct conveyance of the air dispensed into the mouthpiece 4, while the throttling or the closure of the hole 15 respectively directed away from the mouthpiece 4 by means of the extension lugs 11 provided at each union 9, as well as the slots 112 in the baffle-wings 12, ensure an efficient elimination of possible "self-dispensing" phenomena.

Finally, due to the fact that the baffle-wings 12 and extension lugs 11 are provided at each union 9, and the holes 15 are made identical or substantially identical and due to their mutual positioning, the connector member 10 may be coupled on either side of the regulator without requiring any replacement or any change of said connector member while ensuring its perfect operation at all times.

Of course, the invention is not limited to the embodiment herein described and illustrated, but broad changes and modifications, especially of constructional nature, may be made thereto without departing from the basic principle as set forth above and as claimed hereinafter.

Thus, for example, the sealing ring 19 may be omitted, and the sealing may be effected by suitable resilient means of different nature.

I claim:

1. In a breathing apparatus for use with a source of compressed air and provided with a first air-pressure reducing stage, the combination of a regulator provided with a second reducing stage and comprising a first chamber having walls communicating with a mouthpiece and a second chamber communicating with the surroundings, said first and second chamber being separated by a membrane which controls the opening and the closure of a dispensing valve within a connector member between said first and said second air-pressure reducing stages, and in which the said first chamber communicating with the said mouthpiece is provided both on the right-hand and left-hand sides with a mating seat for said connector member between the said two air-pressure reducing stages, the said connector member being provided with two symmetrically formed air-dispensing holes, and in which a closing and/or throttling means is provided at each mating seat for cooperation with whichever one of the said two dispensing holes is disposed away from the mouthpiece said connector member being locked in a pre-established position in its seat by means of a bayonet joint, centering and safety means to prevent accidental disconnection of said member.

2. A regulator according to claim 1, in which baffle means are provided to convey directly into the mouthpiece the air being dispensed through the air-dispensing port of said connector member directed towards the mouthpiece, said baffle means extending so as to overlay at a certain distance, a mouth of a pipe-union) of the mouthpiece and being provided with slots for passing a fraction of the air into the first chamber communicating with the mouthpiece.

3. A regulator according to claim 1, in which the said mating seats are formed by unions co-axial with each other on opposite sides of the first chamber communicating with the mouthpiece and are normal to the longitudinal vertical central plane of the second reducing stage of the regulator.

4. A regulator according to claim 1, in which the closing and/or throttling means at each union is formed by a co-axial extension lug protruding from a wall of the said first chamber away from the said membrane and extending downwards by about one fourth of the perimeter of said union, terminating at the free end thereof in a shoulder ledge for the connector member.

5. A regulator according to claim 2, in which the said baffles at each union are each formed by a baffle-wing provided with slots and protruding from a upper wall of the casing of said first chamber and extending transverse to the longitudinal axis of said first chamber to terminate nearly at the same level as the upper wall of the unions, while they terminate at a short distance from each other at the longitudinal vertical central plane.

6. A regulator according to claim 5, in which the free lower edge and the free edge facing said longitudinal vertical central plane of each baffle wing is slightly bent towards the mouthpiece.

7. A regulator according to claim 1, in which said connector member comprises a cylindrical fit-in portion provided with two dispensing ports and two diametrically-opposite pegs co-operating with the centering and safety means of each union.

8. A regulator according to claim 1, in which for each union the centering and safety means comprises a groove defined at both sides by a ridge shaped as a ratchet tooth, said ridges being arranged so that, upon assembling the connector member, the pegs on the cylindrical portion will slide over said ridges and snappingly engage into the grooves, while the disassembling requires the disengagement of the pegs of the connector member from the groove by depressing the connector member axially towards the first chamber.

9. A regulator according to claim 1, wherein the said mating seats are formed by unions, and in the locked position of the connector member in the groove of each union, the respective extension lug overlaps one port while the other port opens into the space between the mouthpiece and respective baffle-wing.

10. A regulator according to claim 1, in which a plug is provided for closing the union that is not associated with a connector member.

* * * * *